United States Patent [19]

Shibata et al.

[11] Patent Number: 4,981,967
[45] Date of Patent: Jan. 1, 1991

[54] PYRIMIDINE COMPOUNDS AND THEIR USE AS LIQUID CRYSTALS

[75] Inventors: Toshihiro Shibata, Omiya; Masaki Kimura, Tokorozawa, both of Japan

[73] Assignee: Adeka Argus Chemical Co., Ltd., Tokyo, Japan

[21] Appl. No.: 216,367

[22] Filed: Jul. 7, 1988

[30] Foreign Application Priority Data

Jul. 15, 1987 [JP] Japan .................................. 62-176720

[51] Int. Cl.$^5$ ............................................ C07D 239/26
[52] U.S. Cl. ................................................... 544/335
[58] Field of Search ......................................... 544/335

[56] References Cited

U.S. PATENT DOCUMENTS

| | | | |
|---|---|---|---|
| 4,358,393 | 11/1982 | Zaschke et al. | 544/335 |
| 4,367,924 | 1/1983 | Clark et al. | 544/335 |
| 4,784,793 | 11/1988 | Coates et al. | 252/299.62 |

*Primary Examiner*—Mary C. Lee
*Assistant Examiner*—J. Richter
*Attorney, Agent, or Firm*—Frishauf, Holtz, Goodman & Woodward

[57] ABSTRACT

The present invention discloses an optically active pyrimidine compound represented by the following general formula:

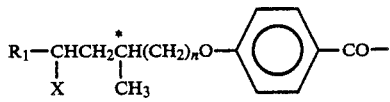
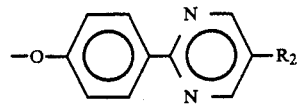

wherein, n is 3 to 5; X is hydrogen atom or chlorine atom; when X is hydrogen atom, $R_1$ is normal alkyl having from 1 to 12 carbon atoms and when X is chlorine atom, $R_1$ is hydrogen atom or normal alkyl having from 1 to 12 carbon atoms; $R_2$ is normal alkyl having from 1 to 18 carbon atoms; and C* represents an asymmetric carbon atom.

10 Claims, No Drawings

PYRIMIDINE COMPOUNDS AND THEIR USE AS LIQUID CRYSTALS

BACKGROUND OF THE INVENTION

1. Field of the Invention

This invention relates to an optically active pyrimidine compound which is a liquid crystal compound useful as an electrooptic element which has excellent properties at high temperature.

2. Description of the Prior Art

Liquid crystals have been employed as various electrooptic elements such as a display device of a watch or an electronic calculator. Most of liquid crystal display devices which have been put into practical use hitherto are those wherein the dielectric orientation effect of a nematicor cholesteric liquid crystal is utilized. However, the application of these liquid crystals to a display device involving a large number of pixels is accompanied by some troubles such as a low response, poor contrast caused by the lack of drive margin and unsatisfactory visual angles. Therefore, there has been frequently attempted to develop a MOS or TFT panel involving formation of a switching device for each pixel.

U.S. Pat. No. 4,367,924 has disclosed a liquid crystal device wherein a smectic phase based on a novel displaying principle is used to thereby overcome the disadvantages as described above.

Further it has been known that a liquid crystal compound exhibiting a C* or H phase consisting of opticallyactive molecules generally has an electrical dipole density P and is ferroelectric. Such a chiral smectic liquid crys-tal having electrical dipoles is more strongly affected by an electric field than dielectric anisotropic ones. As a result, the polarity of P is made parallel to the direction of the electric field. Thus the direction of the moleculescan be controlled by reversing the direction of the applied electric field. Then the average change in the direction of the major axes of these molecules is detected with the use of two polarizing plates. Thus the liquid crystal can be used as an electroopticelement.

The effect of the spontaneous polarization of this electrooptic element, wherein the response of the smectic C* or H phase to an electric field is utilized, and the electric field exert an action $10^3$ to $10^4$ times as high as thoseof dielectric anisotropic ones. Thus the former shows a high-speed response compared with a TN liquid crystal device. Further it is possible to impart thereto a memory function by appropriately controlling the orientation. Therefore itis expected to apply the same to a high-speed optical shutter or to a display of a large capacity.

There have been synthesized various chiral smectic liquid crystal compounds having a ferroelectricity and the properties therefof have been studied.

For example, an optically active 2-(4-alkoxyphenyl)-5-alkylpyrimidine compound has been proposed as a compound which is stable to water and shows a chiral smectic phase within a wide range of temperature in Japanese Patent Laid-Open Nos. 93170/1986 and 129169/1986.

However, each compound as described above is available only within a restricted range of temperature. Namely, itsinsufficient properties, in particular, at a high temperature make it unsatisfactory from the practical viewpoint.

SUMMARY OF THE INVENTION

It is the main object of the present invention to provide a compound useful as a liquid crystal which is suitablefor preparing a composition available over an unlimited temperature range and, in particular, having a liquid crystal temperature at higher temperature.

We have attempted to develop a pyrimidine liquid crystal compound which shows a chiral nematic phase (N*) and/or chiral smectic phase (SmC*) over a wide temperature range. As a result, we have found that an optically activepyrimidine compound of the following general formula, wherein an alkyl group has an asymmetrical carbon atom shows a chiral nematic phase and/or a chiral smectic phase over a wide range of temperature involving, in particular, a high temperature region, thus completing the present invention.

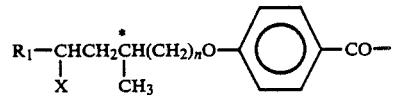

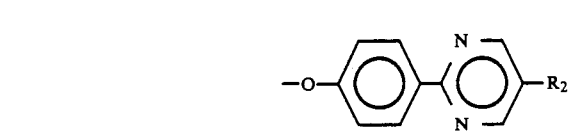

wherein, n is 3 to 5; X is hydrogen atom or chlorine atom; when X is hydrogen atom, $R_1$ is normal alkyl having from 1 to 12 carbon atoms and when X is chlorine atom, $R_1$ is hydrogen atom or normal alkyl having from 1 to 12 carbon atoms; $R_2$ is normal alkyl having from 1 to 18 carbon atoms; and C* represents an asymmetric carbon atom.

DETAILED DESCRIPTION OF THE INVENTION

The compound of the present invention as represented by the above general formula can be prepared by a common methodused in synthesizing phenylpyrimidine compounds.

For example, it may be prepared by esterifying 5-alkyl-2-(4-hydroxyphenyl)pyrimidine with corresponding 4-opticallyactive alkoxy benzoic acid; or by esterifying 4-cyanophenol with corresponding 4-optically active alkoxy benzoic acid and converting the resulting product into pyrimidine in a conventional manner.

A 5-alkyl-2-(4-hydroxyphenyl)pyrimidine compound may be prepared by a conventional method comprising, for example, converting 4-cyanophenol into a benzyl ether in a conventional manner, converting the resulting ether into 4-benzyloxy-benzamidine hydrochloride, reacting the obtained product with an n-alkylmalonic acid diester to give a 2-(4-benzyloxyphenyl)-4,6-dihydroxy-5-n-alkylpyrimidine and then thenchlorinating and reducing the product.

The obtained compound of the present invention as represented by the above general formula can be used alone as a liquid crystal material. Alternately it can be mixed with other liquid crystal compound(s).

To further illustrate the present invention, the following Examples will be given.

EXAMPLE 1

Synthesis of (R)-4-(6'-chloro-4'-methylhexyloxy) benzoic acid 4-(5'-n-octyl-2'-pyrimidinyl)phenyl ester

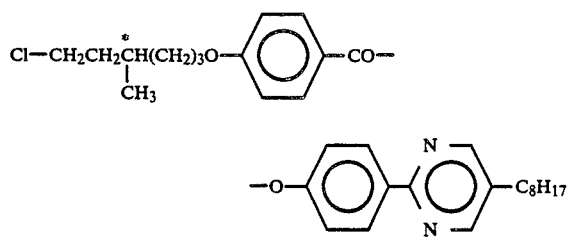

1.08 g of (R)-4-(6'-chloro-4'-methylhexyloxy)benzoic acid ($[\alpha]_D = +5.00°$, C=1, at 25° C., CHCl$_3$ solution), 1.14 g of 4-(5'-n-octyl-2'-pyrimidinyl)phenol, 0.83 g of N,N'-dicyclohexylcarbodiimide, 0.08 g of 4-pyrrolidinopyridine and 20 ml of dichloromethane were stirred for three hours at room temperature.

The precipitated dicyclohexylurea were filtered and 2.59 g of crude product was obtained by removal of solvent.

The product was purified on a silica gel column with the use of hexane/ethylacetate (85/15) as a developing solvent. Thus 1.79 g of (R)-4-(6'-chloro-4'-methylhexyloxy) benzoic acid 4-(5'-n-octyl-2'-pyrimidinyl)phenyl ester was obtained.

Infrared spectroscopy (cm$^{-1}$) 2900(s), 2850(s), 1725(s), 1600(s), 1580(m), 1540(vw), 1510(m), 1460(m), 1430(s), 1385(vw), 1310(m), 1250(vs), 1200(s), 1160(s), 1075(m), 1055(m), 1010(m), 885(m), 845(m), 790(m), 760(m), 720(w), 685(w), 650(m), 550(vw), 505(vw) and 475(vw).

Optical rotation $[\alpha]_D = +3.64°$ (C=1, CHCl$_3$ solution, 26° C.).

This compound was poured into a transparent glass cell and the following phase transition was observed under a polarization microscope.

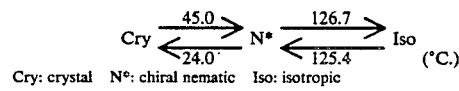

Cry: crystal   N*: chiral nematic   Iso: isotropic

It has been confirmed that the above compound of the present invention shows an N* phase over a wide temperature range involving a temperature higher than 120° C., which obviously suggests that it is suitable for the preparation of a composition showing a high liquid crystal temperature.

EXAMPLE 2

Synthesis of (R)-4-(6'-chloro-4'-methylnonyloxy) benzoic acid 4-(5'-n-decyl-2'-pyrimidinyl)phenyl ester

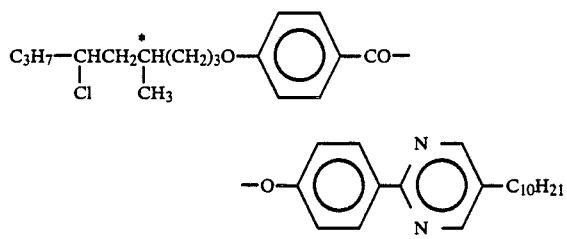

The procedure of Example 1 was followed using 1.25 g of (R)-4-(6'-chloro-4'-methylnonyloxy)benzoic acid ($[\alpha]_D = +3.37°$, C=1, at 23° C., CHCl$_3$ solution) and 1.26 g of 4-(5'-n-decyl-2'-pyrimidinyl)phenol and 2.70 g of crude product was obtained.

The product was purified on a silica gel column with the use of hexane/ethylacetate (90/10) as a developing solvent. Thus 2.08 g of (R)-4-(6'-chloro-4'-methylnonyloxy) benzoic acid 4-(5'-n-decyl-2'-pyrimidinyl)phenyl ester was obtained.

Infrared spectroscopy (cm$^{-1}$) 2900(s), 2850(s), 1720(s), 1600(s), 1585(m), 1545(w), 1510(w), 1460(m), 1425(s), 1380(vw), 1310(vw), 1250(vs), 1200(s), 1165(s), 1075(m), 1055(m), 1010(m), 930(vw), 885(w), 845(m), 790(m), 760(m), 720(vw), 690(vw), 650(w), 610(vw), 550(vw) and 510(vw).

Optical rotation $[\alpha]_D = +2.64°$ (C=1, CHCl$_3$ solution, 26° C.).

This compound was poured into a transparent glass electrode cell of 2 μm in thickness, which had been subjected to orientation by rubbing, and heated to 140° C. to thereby give an isotropic liquid.

The liquid crystal cell thus obtained was cooled under a crossed Nicol prism while applying rectangular pulses (15 V. 1 Hz) thereto. As a result, definite switching behaviors were observed from 66.1 to −3° C.

The following phase transition was observed under a polarization microscope.

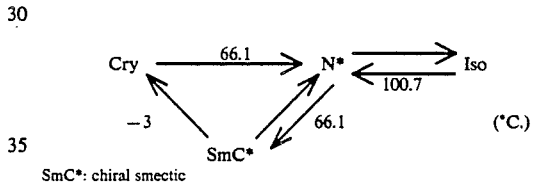

SmC*: chiral smectic

It has been confirmed that the above compound of the present invention shows an N* phase over 100° C. and SmC* phase at 66° C., which obviously suggests that it is suitable for the preparation of a composition showing a high liquid crystal temperature.

EXAMPLE 3

Synthesis of (S)-4-(4'-methyloctoxy)benzoic acid 4-(5'-n-decyl-2'-pyrimidinyl)phenyl ester

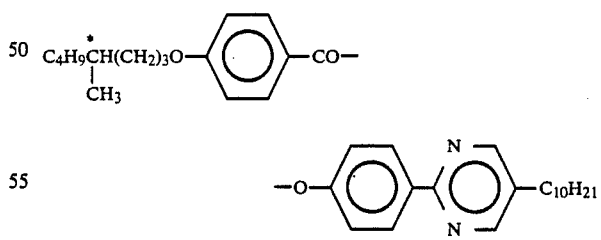

The procedure of Example 1 was followed using 1.06 g of (S)-4-(4'-methyloctoxy)benzoic acid ($[\alpha]_D = +3.53°$, C=1, at 26° C., CHCl$_3$ solution) and 1.25 g of 4-(5'-n-decyl-2'-pyrimidinyl)phenol, and 2.25 g of crude product was obtained.

The product was purified on a silica gel column with the use of hexane/ethylacetate (90/10) as a developing solvent. Thus 1.82 g of (S)-4-(4'-methyloctoxy)benzoic acid 4-(5'-n-decyl-2'-pyrimidinyl)phenyl ester was obtained.

Infrared spectroscopy (cm$^{-1}$) 2900(s), 2850(s), 1720(s), 1600(s), 1580(m), 1540(vw), 1510(m), 1460(m), 1425(s), 1375(vw), 1310(m), 1250(vs), 1200(s), 1165(s), 1075(m), 1055(m), 1010(m), 930(vw), 880(w), 840(m), 790(m), 760(m), 720(vw), 690(w), 650(w), 550(vw) and 505(vw).

Optical rotation $[\alpha]_D = +2.64°$ (C=1, CHCl$_3$ solution, 26° C.)

This compound was poured into a transparent glass electrode cell of 2 μm in thickness, which had been subjected to orientation by rubbing, and heated to 140° C. to thereby give an isotropic liquid.

The liquid crystal cell thus obtained was cooled under a crossed Nicol prism while applying rectangular pulses (15 V. 1 Hz) thereto. As a result, definite switching behaviors were observed from 85.1° to 2° C.

The following phase transition was observed under a polarization microscope.

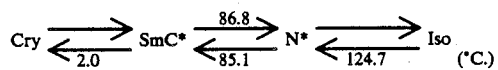

It has been confirmed that the above compound of the present invention shows an N* phase over 100° C. and SmC* phase at 66° C., which obviously suggests that it is suitable for the preparation of a composition showing a high liquid crystal temperature.

EXAMPLE 4

Synthesis of (S)-4-(6'-methyldecyloxy)benzoic acid 4-(5'-n-decyl-2'-pyrimidinyl)phenyl ester

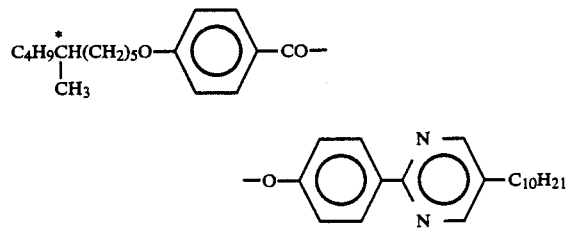

The procedure of Example 1 was followed using 1.17 g of (S)-4-(6'-methyldecyloxy)benzoic acid ($[\alpha]_D = +1.70°$, C=1, at 26° C., CHCl$_3$ solution) and 1.25 g of 4-(5'-n-decyl-2'-pyrimidinyl)phenol and 2.13 g of crude product was obtained. The product was purified on a silica gel column with the use of hexane/ethylacetate (85/15) as a developing solvent followed by recrystalization from ethanol/acetone (80/20). Thus 1.48 g of (S)-4-(6'-methyldecyloxy)benzoic acid 4-(5'-n-decyl-2'-pyrimidinyl)phenyl ester was obtained.

Infrared spectroscopy (cm$^{-1}$) 2900(s), 2850(s), 1725(s), 1605(s), 1590(s), 1545(w), 1510(m), 1460(m), 1430(s), 1390(vw), 1375(vw), 1310(w), 1250(vs), 1200(s), 1170(s), 1110(vw), 1075(m), 1060(m), 1010(m), 960(vw), 880(vw), 845(m), 790(m), 760(m), 720(vw), 690(w), 655(m) and 505(vw).

Optical rotation $[\alpha]_D = +3.71°$ (C=1, CHCl$_3$ solution, 26° C.).

This compound was poured into a transparent glass electrode cell of 2 μm in thickness, which had been subjected to orientation by rubbing, and heated to 140° C. to thereby give an isotropic liquid.

The liquid crystal cell thus obtained was cooled under a crossed Nicol prism while applying rectangular pulses (15 V. 1 Hz) thereto. As a result, definite switching behaviorswere observed from 102.7° to 20.9° C.

The following phase transition was observed under a polarization microscope.

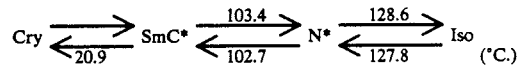

It has been confirmed that the above compound of the present invention shows an N* phase over 100° C. and SmC* phase at 66° C., which obviously suggests that it is suitable for the preparation of a composition showing a high liquid crystal temperature.

What is claimed is:

1. An optically active pyrimidine compound represented by the following general formula:

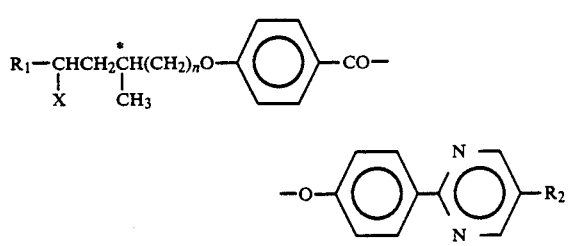

wherein, n is 3 to 5; X is a hydrogen atom or a chlorine atom; when X is a hydrogen atom, R$_1$ is straight chain alkyl having from 1 to 12 carbon atoms and when X is a chlorine atom, R is a hydrogen atom or straight chain alkyl having from 1 to 12 carbon atoms; R$_2$ is straight chain alkyl having from 1 to 18 carbon atoms; and C* represents an asymmetric carbon atom.

2. A pyrimidine compound as set forth in claim 1 in which X is chlorine atom.

3. A pyrimidine compound as set forth in claim 1 in which X is hydrogen atom.

4. A pyrimidine compound as set forth in claim 1, in which R$_2$ is straight chain alkyl having from 6 to 12 carbon atoms.

5. A pyrimidine compound as set forth in claim 1 represented by the following formula:

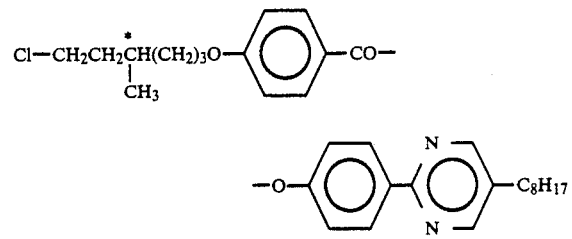

6. A pyrimidine compound as set forth in claim 1 represented by the following formula:

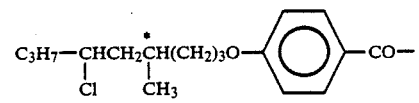

-continued

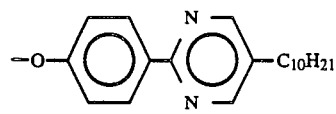

7. A pyrimidine compound as set forth in claim 1 represented by the following formula:

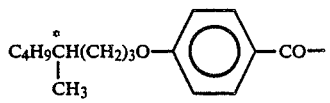

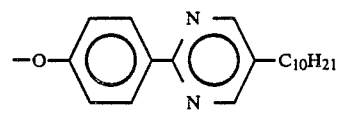

8. A pyrimidine compound as set forth in claim 1 represented by the following formula:

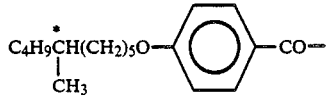

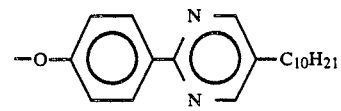

9. A pyrimidine compound as set forth in claim 2 in which $R_2$ is straight chain alkyl having from 5 to 12 carbon atoms.

10. A pyrimidine compound as set forth in claim 3 in which $R_2$ is straight chain alkyl having from 5 to 12 carbon atoms.

* * * * *